US010568518B2

(12) United States Patent
Zott et al.

(10) Patent No.: US 10,568,518 B2
(45) Date of Patent: *Feb. 25, 2020

(54) DEVICE FOR DETECTING AND ILLUMINATING THE VASCULATURE USING AN FPGA

(71) Applicant: AccuVein, Inc., Cold Spring Harbor, NY (US)

(72) Inventors: Joseph Zott, Menlo Park, CA (US); Fred Wood, Medford, NY (US); Dimitry Yavid, Stony Brook, NY (US); Seung P. Kim, San Francisco, CA (US); Klaus Zietlow, Piedmont, CA (US)

(73) Assignee: AccuVein, Inc., Cold Spring Harbor, NY (US)

( * ) Notice: Subject to any disclaimer, the term of this patent is extended or adjusted under 35 U.S.C. 154(b) by 281 days.

This patent is subject to a terminal disclaimer.

(21) Appl. No.: 15/679,277

(22) Filed: Aug. 17, 2017

(65) Prior Publication Data

US 2018/0070832 A1 Mar. 15, 2018

Related U.S. Application Data

(63) Continuation of application No. 14/723,674, filed on May 28, 2015, now Pat. No. 9,782,079, which is a (Continued)

(51) Int. Cl.
*A61B 5/00* (2006.01)
*A61B 5/02* (2006.01)
*A61B 5/107* (2006.01)

(52) U.S. Cl.
CPC ............ *A61B 5/0082* (2013.01); *A61B 5/004* (2013.01); *A61B 5/0033* (2013.01); *A61B 5/02007* (2013.01); *A61B 5/1075* (2013.01); *A61B 5/1077* (2013.01); *A61B 5/1079* (2013.01); *A61B 5/742* (2013.01); *A61B 5/743* (2013.01); *A61B 5/745* (2013.01)

(58) Field of Classification Search
None
See application file for complete search history.

(56) References Cited

U.S. PATENT DOCUMENTS 3,136,310 A  6/1964  Meltzer
3,349,762 A  10/1967  Kapany
(Continued)

FOREIGN PATENT DOCUMENTS

FR  2289149  5/1976
GB  1298707  12/1972
(Continued)

OTHER PUBLICATIONS

Wiklof, Chris, "Display Technology Spawns Laser Camera," LaserFocusWorld, Dec. 1, 2004, vol. 40, Issue 12, PennWell Corp., USA.
(Continued)

*Primary Examiner* — James M Kish
(74) *Attorney, Agent, or Firm* — Thomas A. O'Rourke; Bodner & O'Rourke, LLP

(57) ABSTRACT

A laser based vascular illumination system utilizing a FPGA for detecting vascular positions, processing an image of such vasculature positions, and projecting the image thereof onto the body of a patient.

23 Claims, 8 Drawing Sheets

Related U.S. Application Data continuation of application No. 13/957,767, filed on Aug. 2, 2013, now Pat. No. 9,072,426.

(60) Provisional application No. 61/678,726, filed on Aug. 2, 2012.

(56) References Cited

U.S. PATENT DOCUMENTS

| | | |
|---|---|---|
| 3,511,227 A | 5/1970 | Stern |
| 3,527,932 A | 9/1970 | Thomas |
| 3,818,129 A | 6/1974 | Yamamoto |
| 3,984,629 A | 10/1976 | Gorog |
| 4,030,209 A | 6/1977 | Dreidling |
| 4,057,784 A | 11/1977 | Tafoya |
| 4,109,647 A | 8/1978 | Stern |
| 4,162,405 A | 7/1979 | Chance |
| 4,182,322 A | 1/1980 | Miller |
| 4,185,808 A | 1/1980 | Donohoe et al. |
| 4,213,678 A | 7/1980 | Pomerantzeff |
| 4,265,227 A | 5/1981 | Ruge |
| 4,312,357 A | 1/1982 | Andersson et al. |
| 4,315,318 A | 2/1982 | Kato |
| 4,321,930 A | 3/1982 | Jobsis et al. |
| 4,393,366 A | 7/1983 | Hill |
| 4,495,949 A | 1/1985 | Stoller |
| 4,502,075 A | 2/1985 | DeForest et al. |
| 4,510,938 A | 4/1985 | Jobsis |
| 4,536,790 A | 8/1985 | Kruger |
| 4,565,968 A | 1/1986 | Macovski |
| 4,567,896 A | 2/1986 | Barnea |
| 4,576,175 A | 3/1986 | Epstein |
| 4,586,190 A | 4/1986 | Tsuji |
| 4,590,948 A | 5/1986 | Nilsson |
| 4,596,254 A | 6/1986 | Adrian |
| 4,619,249 A | 10/1986 | Landry |
| 4,669,467 A | 6/1987 | Willet |
| 4,697,147 A | 9/1987 | Moran |
| 4,699,149 A | 10/1987 | Rice |
| 4,703,758 A | 11/1987 | Omura |
| 4,766,299 A | 8/1988 | Tierney et al. |
| 4,771,308 A | 9/1988 | Tejima et al. |
| 4,780,919 A | 11/1988 | Harrison |
| 4,799,103 A | 1/1989 | Mucherheide |
| 4,817,622 A | 4/1989 | Pennypacker et al. |
| 4,846,183 A | 7/1989 | Martin |
| 4,862,894 A | 9/1989 | Fujii |
| 4,899,756 A | 2/1990 | Sonek |
| 4,901,019 A | 2/1990 | Wedeen |
| 4,926,867 A | 5/1990 | Kanda |
| RE33,234 E | 6/1990 | Landry |
| 4,938,205 A | 7/1990 | Nudelman |
| 5,074,642 A | 12/1991 | Hicks |
| 5,088,493 A | 2/1992 | Giannini |
| 5,103,497 A | 4/1992 | Hicks |
| 5,146,923 A | 9/1992 | Dhawan |
| 5,174,298 A | 12/1992 | Dolfi |
| 5,184,188 A | 2/1993 | Bull |
| 5,214,458 A | 5/1993 | Kenai |
| 5,222,495 A | 6/1993 | Clarke |
| 5,261,581 A | 11/1993 | Harden |
| 5,293,873 A | 3/1994 | Fang |
| 5,339,817 A | 8/1994 | Nilsson |
| 5,371,347 A | 12/1994 | Plesko |
| 5,406,070 A | 4/1995 | Edgar et al. |
| 5,418,546 A | 5/1995 | Nakagakiuchi et al. |
| 5,423,091 A | 6/1995 | Lange |
| 5,436,655 A | 7/1995 | Hiyama |
| D362,910 S | 10/1995 | Creaghan |
| 5,455,157 A | 10/1995 | Hinzpeter et al. |
| 5,494,032 A | 2/1996 | Robinson |
| 5,497,769 A | 3/1996 | Gratton |
| 5,504,316 A | 4/1996 | Bridgelall et al. |
| 5,519,208 A | 5/1996 | Esparza et al. |
| 5,541,820 A | 7/1996 | McLaughlin |
| 5,542,421 A | 8/1996 | Erdman |
| 5,598,842 A | 2/1997 | Ishihara et al. |
| 5,603,328 A | 2/1997 | Zucker et al. |
| 5,608,210 A | 3/1997 | Esparza et al. |
| 5,610,387 A | 3/1997 | Bard et al. |
| 5,625,458 A | 4/1997 | Alfano |
| 5,631,976 A | 5/1997 | Bolle et al. |
| 5,655,530 A | 8/1997 | Messerschmidt |
| 5,678,555 A | 10/1997 | O'Connell |
| 5,716,796 A | 2/1998 | Bull |
| 5,719,399 A | 2/1998 | Alfano et al. |
| 5,747,789 A | 5/1998 | Godik |
| 5,756,981 A | 5/1998 | Roustaei et al. |
| 5,758,650 A | 6/1998 | Miller |
| 5,772,593 A | 6/1998 | Hakamata |
| 5,787,185 A | 7/1998 | Clayden |
| 5,814,040 A | 9/1998 | Nelson |
| 5,836,877 A | 11/1998 | Zavislan |
| 5,847,394 A | 12/1998 | Alfano et al. |
| 5,860,967 A | 1/1999 | Zavislan et al. |
| 5,929,443 A | 7/1999 | Alfano et al. |
| 5,946,220 A | 8/1999 | Lemelson |
| 5,947,906 A | 9/1999 | Dawson, Jr. et al. |
| 5,966,204 A | 10/1999 | Abe |
| 5,969,754 A | 10/1999 | Zeman |
| 5,982,553 A | 11/1999 | Bloom et al. |
| 5,988,817 A | 11/1999 | Mizushima et al. |
| 5,995,856 A | 11/1999 | Manheimer et al. |
| 5,995,866 A | 11/1999 | Lemelson |
| 6,006,126 A | 12/1999 | Cosman |
| 6,032,070 A | 2/2000 | Flock et al. |
| 6,056,692 A | 5/2000 | Schwartz |
| 6,061,583 A | 5/2000 | Ishihara et al. |
| 6,101,036 A | 8/2000 | Bloom |
| 6,122,042 A | 9/2000 | Wunderman |
| 6,132,379 A | 10/2000 | Patacsil |
| 6,135,599 A | 10/2000 | Fang |
| 6,141,985 A | 11/2000 | Cluzeau et al. |
| 6,142,650 A | 11/2000 | Brown et al. |
| 6,149,644 A | 11/2000 | Xie |
| 6,171,301 B1 | 1/2001 | Nelson |
| 6,178,340 B1 | 1/2001 | Svetliza |
| 6,230,046 B1 | 5/2001 | Crane et al. |
| 6,240,309 B1 | 5/2001 | Yamashita |
| 6,251,073 B1 | 6/2001 | Imran et al. |
| 6,263,227 B1 | 7/2001 | Boggett et al. |
| 6,301,375 B1 | 10/2001 | Choi |
| 6,305,804 B1 | 10/2001 | Rice |
| 6,314,311 B1 | 11/2001 | Williams et al. |
| 6,334,850 B1 | 1/2002 | Amano et al. |
| 6,353,753 B1 | 3/2002 | Flock |
| 6,424,858 B1 | 7/2002 | Williams |
| 6,436,655 B1 | 8/2002 | Bull |
| 6,438,396 B1 | 8/2002 | Cook et al. |
| 6,463,309 B1 | 10/2002 | Ilia |
| 6,464,646 B1 | 10/2002 | Shalom et al. |
| 6,523,955 B1 | 2/2003 | Eberl |
| 6,542,246 B1 | 4/2003 | Toida |
| 6,556,854 B1 | 4/2003 | Sato et al. |
| 6,556,858 B1 | 4/2003 | Zeman |
| 6,599,247 B1 | 7/2003 | Stetten |
| 6,631,286 B2 | 10/2003 | Pfeiffer |
| 6,648,227 B2 | 11/2003 | Swartz et al. |
| 6,650,916 B2 | 11/2003 | Cook et al. |
| 6,689,075 B2 | 2/2004 | West |
| 6,690,964 B2 | 2/2004 | Bieger et al. |
| 6,702,749 B2 | 3/2004 | Paladini et al. |
| 6,719,257 B1 | 4/2004 | Greene et al. |
| 6,755,789 B2 | 6/2004 | Stringer |
| 6,777,199 B2 | 8/2004 | Bull |
| 6,782,161 B2 | 8/2004 | Barolet et al. |
| 6,845,190 B1 | 1/2005 | Smithwick |
| 6,882,875 B1 | 4/2005 | Crowley |
| 6,889,075 B2 | 5/2005 | Marchitto et al. |
| 6,913,202 B2 | 7/2005 | Tsikos et al. |
| 6,923,762 B1 | 8/2005 | Creaghan |
| 6,980,852 B2 | 12/2005 | Jersey-Willuhn et al. |
| 7,092,087 B2 | 8/2006 | Kumar |
| 7,113,817 B1 | 9/2006 | Winchester |
| 7,158,660 B2 | 1/2007 | Gee et al. |

(56) References Cited

U.S. PATENT DOCUMENTS

| | | |
|---|---|---|
| 7,158,859 B2 | 1/2007 | Wang |
| 7,225,005 B2 | 5/2007 | Kaufman et al. |
| 7,227,611 B2 | 6/2007 | Hull et al. |
| 7,239,909 B2 | 7/2007 | Zeman |
| 7,247,832 B2 | 7/2007 | Webb |
| 7,280,860 B2 | 10/2007 | Ikeda et al. |
| 7,283,181 B2 | 10/2007 | Allen |
| 7,302,174 B2 | 11/2007 | Tan et al. |
| 7,333,213 B2 | 2/2008 | Kempe |
| D566,283 S | 4/2008 | Brafford et al. |
| 7,359,531 B2 | 4/2008 | Endoh et al. |
| 7,376,456 B2 | 5/2008 | Marshik-Geurts |
| 7,431,695 B1 | 10/2008 | Creaghan |
| 7,532,746 B2 | 5/2009 | Marcotte et al. |
| 7,545,837 B2 | 6/2009 | Oka |
| 7,559,895 B2 | 7/2009 | Stetten |
| 7,579,592 B2 | 8/2009 | Kaushal |
| 7,608,057 B2 | 10/2009 | Woehr et al. |
| 7,699,776 B2 | 4/2010 | Walker et al. |
| 7,708,695 B2 | 5/2010 | Akkermans |
| 7,792,334 B2 | 9/2010 | Cohen |
| 7,846,103 B2 | 12/2010 | Cannon, Jr. |
| 7,904,138 B2 | 3/2011 | Goldman |
| 7,904,139 B2 | 3/2011 | Chance |
| 7,925,332 B2 | 4/2011 | Crane et al. |
| 7,966,051 B2 | 6/2011 | Xie |
| 8,032,205 B2 | 10/2011 | Mullani |
| 8,078,263 B2 | 12/2011 | Zeman et al. |
| 8,187,189 B2 | 5/2012 | Jung et al. |
| 8,199,189 B2 | 6/2012 | Kagenow et al. |
| 8,320,998 B2 | 11/2012 | Sato |
| 8,336,839 B2 | 12/2012 | Boccoleri et al. |
| 8,364,246 B2 | 1/2013 | Thierman |
| 8,467,855 B2 | 6/2013 | Yasui |
| 8,494,616 B2 | 7/2013 | Zeman |
| 8,498,694 B2 | 7/2013 | McGuire, Jr. et al. |
| 8,509,495 B2 | 8/2013 | Xu et al. |
| 8,548,572 B2 | 10/2013 | Crane et al. |
| 8,630,465 B2 | 1/2014 | Wieringa |
| 8,649,848 B2 | 2/2014 | Crane et al. |
| 2001/0006426 A1 | 7/2001 | Son |
| 2001/0056237 A1 | 12/2001 | Cane |
| 2002/0016533 A1 | 2/2002 | Marchitto |
| 2002/0118338 A1 | 8/2002 | Kohayakawa |
| 2002/0188203 A1 | 12/2002 | Smith |
| 2003/0018271 A1 | 1/2003 | Kimble |
| 2003/0052105 A1 | 3/2003 | Nagano |
| 2003/0120154 A1 | 6/2003 | Sauer |
| 2003/0125629 A1 | 7/2003 | Ustuner |
| 2003/0156260 A1 | 8/2003 | Putilin |
| 2004/0015158 A1 | 1/2004 | Chen et al. |
| 2004/0022421 A1 | 2/2004 | Endoh et al. |
| 2004/0046031 A1 | 3/2004 | Knowles et al. |
| 2004/0171923 A1 | 9/2004 | Kalafut et al. |
| 2004/0222301 A1 | 11/2004 | Willins et al. |
| 2005/0017924 A1 | 1/2005 | Utt et al. |
| 2005/0033145 A1 | 2/2005 | Graham et al. |
| 2005/0043596 A1 | 2/2005 | Chance |
| 2005/0047134 A1 | 3/2005 | Mueller et al. |
| 2005/0085802 A1 | 4/2005 | Gruzdev |
| 2005/0113650 A1 | 5/2005 | Pacione et al. |
| 2005/0131291 A1 | 6/2005 | Floyd et al. |
| 2005/0135102 A1 | 6/2005 | Gardiner et al. |
| 2005/0141069 A1 | 6/2005 | Wood et al. |
| 2005/0143662 A1 | 6/2005 | Marchitto et al. |
| 2005/0146765 A1 | 7/2005 | Turner |
| 2005/0154303 A1 | 7/2005 | Walker |
| 2005/0157939 A1 | 7/2005 | Arsenault et al. |
| 2005/0161051 A1 | 7/2005 | Pankratov et al. |
| 2005/0168980 A1 | 8/2005 | Dryden et al. |
| 2005/0174777 A1 | 8/2005 | Cooper et al. |
| 2005/0175048 A1 | 8/2005 | Stern et al. |
| 2005/0187477 A1 | 8/2005 | Serov |
| 2005/0215875 A1 | 9/2005 | Khou |
| 2005/0265586 A1 | 12/2005 | Rowe et al. |
| 2005/0281445 A1 | 12/2005 | Marcotte et al. |
| 2006/0007134 A1 | 1/2006 | Ting |
| 2006/0020212 A1 | 1/2006 | Xu |
| 2006/0025679 A1 | 2/2006 | Viswanathan et al. |
| 2006/0052690 A1 | 3/2006 | Sirohey et al. |
| 2006/0081252 A1 | 4/2006 | Wood |
| 2006/0100523 A1 | 5/2006 | Ogle |
| 2006/0103811 A1 | 5/2006 | May et al. |
| 2006/0122515 A1 | 6/2006 | Zeman |
| 2006/0129037 A1 | 6/2006 | Kaufman et al. |
| 2006/0129038 A1 | 6/2006 | Zelenchuk et al. |
| 2006/0151449 A1 | 7/2006 | Warner |
| 2006/0173351 A1 | 8/2006 | Marcotte et al. |
| 2006/0184040 A1 | 8/2006 | Keller et al. |
| 2006/0206027 A1 | 9/2006 | Malone |
| 2006/0232660 A1 | 10/2006 | Nakajima et al. |
| 2006/0253010 A1 | 11/2006 | Brady et al. |
| 2006/0271028 A1 | 11/2006 | Altshuler et al. |
| 2007/0016079 A1 | 1/2007 | Freeman et al. |
| 2007/0070302 A1 | 3/2007 | Govorkov |
| 2007/0115435 A1 | 5/2007 | Rosendaal |
| 2007/0176851 A1 | 8/2007 | Wiley |
| 2008/0045841 A1 | 2/2008 | Wood et al. |
| 2008/0147147 A1 | 6/2008 | Griffiths et al. |
| 2008/0194930 A1 | 8/2008 | Harris et al. |
| 2009/0018414 A1 | 1/2009 | Toofan |
| 2009/0171205 A1 | 7/2009 | Kharin |
| 2010/0051808 A1 | 3/2010 | Zeman et al. |
| 2010/0061598 A1 | 3/2010 | Seo |
| 2010/0087787 A1 | 4/2010 | Woehr et al. |
| 2010/0177184 A1 | 7/2010 | Berryhill et al. |
| 2010/0312120 A1 | 12/2010 | Meier |
| 2014/0039309 A1 | 2/2014 | Harris et al. |
| 2014/0046291 A1 | 2/2014 | Harris et al. |

FOREIGN PATENT DOCUMENTS

| | | |
|---|---|---|
| GB | 1507329 | 4/1978 |
| JP | S60-108043 A | 6/1985 |
| JP | 04-042944 | 2/1992 |
| JP | 07-255847 | 10/1995 |
| JP | 08023501 A | 1/1996 |
| JP | 08-164123 | 6/1996 |
| JP | 2000/316866 A | 11/2000 |
| JP | 2002 328428 A | 11/2002 |
| JP | 2002/345953 A | 12/2002 |
| JP | 2004 237051 | 8/2004 |
| JP | 2004/329786 A | 11/2004 |
| KR | 2003/0020152 A | 11/2004 |
| WO | WO 1994 22370 | 10/1994 |
| WO | WO 1996 39925 | 12/1996 |
| WO | WO 9826583 | 6/1998 |
| WO | WO 99/48420 | 9/1999 |
| WO | WO 2001 82786 | 11/2001 |
| WO | WO 2003 009750 | 2/2003 |
| WO | WO 2005/053773 | 6/2005 |
| WO | WO 2007078447 | 7/2007 |

OTHER PUBLICATIONS

Nikbin, Darius, "IPMS Targets Colour Laser Projectors," Optics & Laser Europe, Mar. 2006, Issue 137, p. 11.

http://sciencegeekgirl.wordpress, com/category/science-myths/page/2/ Myth 7: Blood is Blue.

http://www exploratorium.edu/sports/hnds_up/hands6.html "Hands Up! To Do & Notice: Getting the Feel of Your Hand".

http://www.wikihow.com/See-Blood-Veins-in-Your-Hand-With-a-Flashlight "How to See Blood Veins in Your Hand With a Flashlight".

Vein Algo Architecture

2-D Moving Window Sum Generator

Latency = X-Sum Buffer Size + Y-Sum Buffer Size

X-Sum Buffer Size = (boxsize - 1)*(number_of_horizontal_pixels) ;
Y-Sum Buffer Size = (boxsize - 1);

DEVICE FOR DETECTING AND ILLUMINATING THE VASCULATURE USING AN FPGA

CROSS REFERENCE TO RELATED APPLICATIONS

This application is a continuation of U.S. application Ser. No. 14/723,674, filed on May 28, 2015, which is a continuation of U.S. application Ser. No. 13/957,767, filed on Aug. 2, 2013, now issued as U.S. Pat. No. 9,072,426, which claims priority on U.S. Provisional Application Ser. No. 61/678,726, filed on Aug. 2, 2012, with the disclosures of each incorporated herein by reference.

BACKGROUND

Summary

A laser based vascular illumination system utilizing a FPGA for detecting vascular positions, processing an image of such vasculature positions, and projecting the image thereof onto the body of a patient.

BRIEF DESCRIPTION

FIG. 1 Block diagram of a system for detecting and illuminating the vasculature in a patient.

Figure 2:
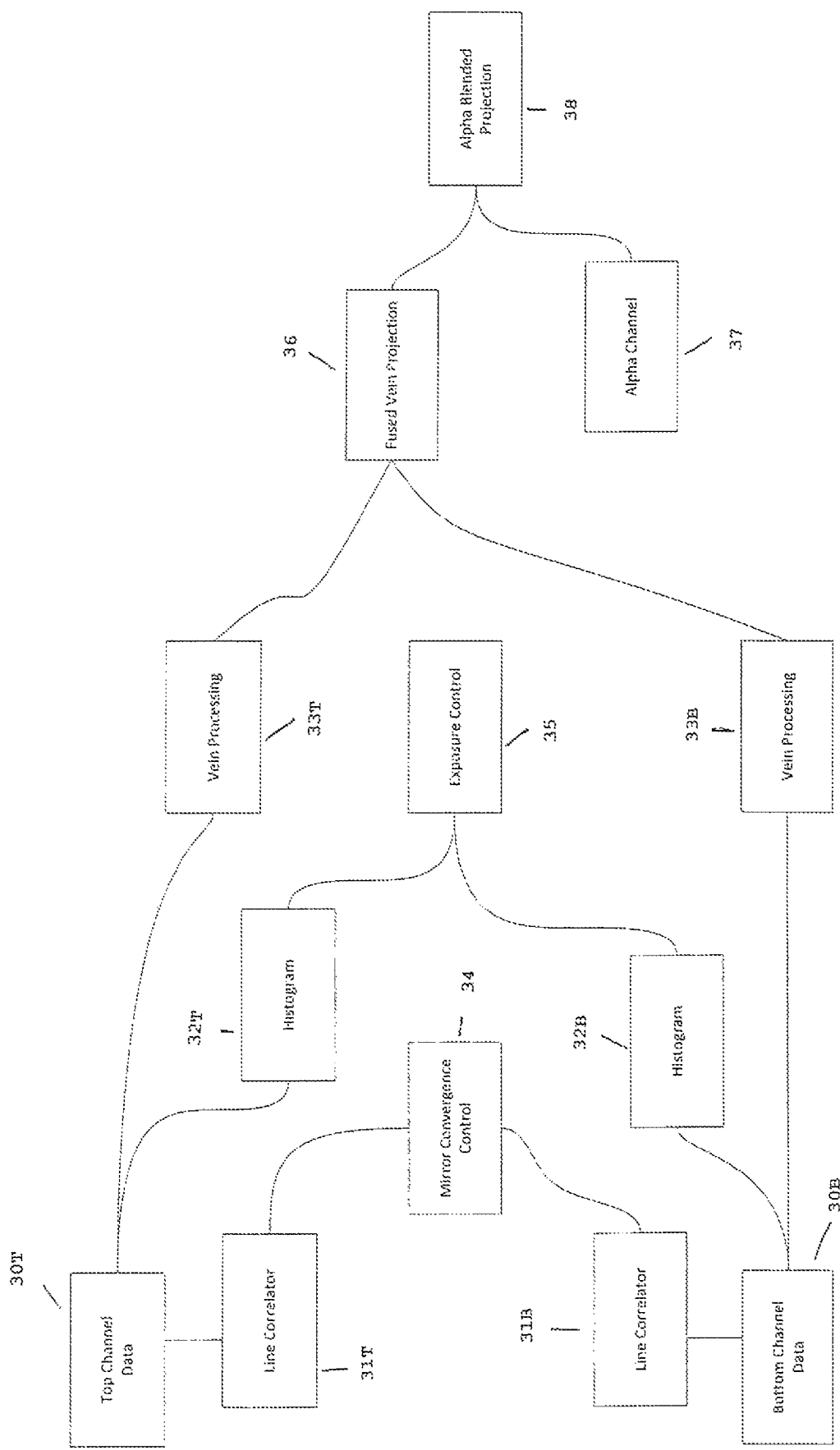
FIG. 2 Shows the signal processing flow of the FPGA.
Figure 7:
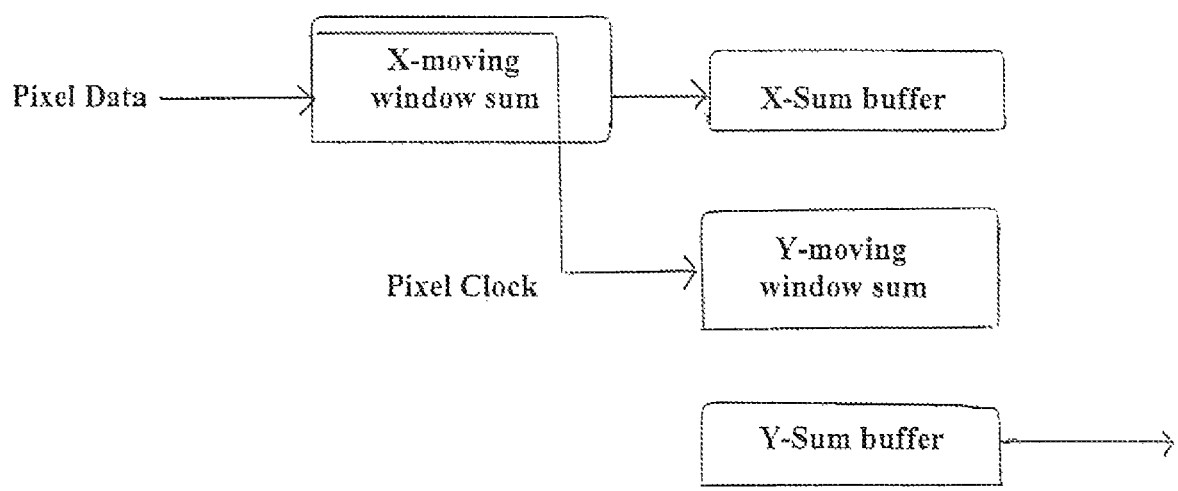

FIG. 7 2-D Moving Window Sum Generator.

Figure 8:
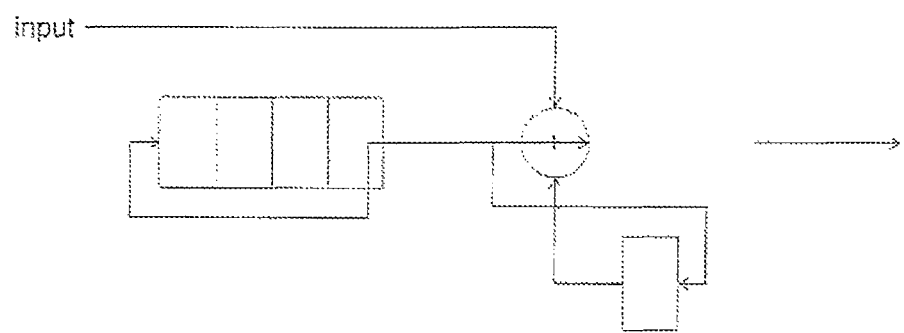

FIG. 8 shows a X-sum generator.

DETAILED DESCRIPTION

Figure 1:
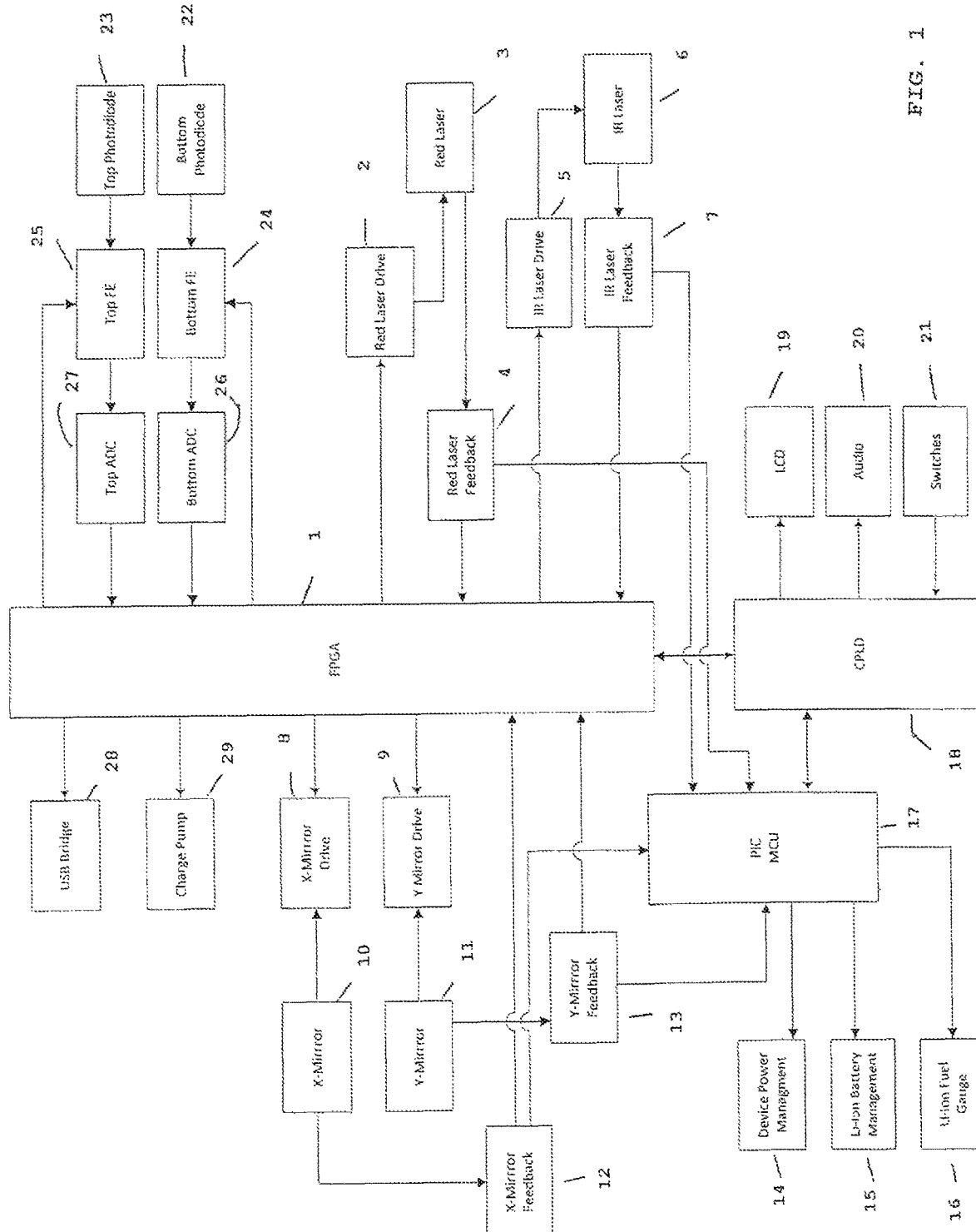

FIG. 1 shows a block diagram of a system for detecting and illuminating the vasculature in a patient.

The system shown in the block diagram of FIG. 1 is used for detecting the location of veins on a patient and illuminating the veins.

The disclosures of U.S. patent application Ser. No. 12/804,506, now issued as U.S. Pat. No. 8,463,364 are incorporated herein by reference.

In a preferred embodiment, FIGS. 30-47 of application Ser. No. 12/804,506 illustrates an assembly of a housing that may be used in the present invention. In the present invention, circuit boards 43, 44 and 15 of application Ser. No. 12/804,506 may be modified to contain the circuitry described by the block diagram in FIG. 1. The remainder of the device in FIGS. 30-47 can remain substantially the same.

In FIG. 1 an FPGA 1 (field programmable gate array) is configured to control a red laser drive 2 which in turn drives a red laser 3. The output of the red laser 3 is controlled in a manner so as to illuminate the detected veins. A red laser feedback 4 detects the output of the red laser 3 and sends the information to the FPGA 1. Accordingly, a closed loop is formed whereby the FPGA 1 can both drive the Red laser 3 and receive feedback as to the red laser 3 state.

FPGA 1 outputs data to an IR laser drive 5 which in turn drives an IR laser 6. The output of the IR laser 6 is controlled to output an intensity of IR light, aimed at the area of the body where veins are located, sufficient to detect the veins.

An IR laser feedback 7 detects the output of the IR laser 6 and sends the information to the FPGA 1. Accordingly, a closed loop is formed whereby the FPGA 1 can both drive the IR Laser 6 and receive feedback as to the IR laser 6 state.

FPGA 1 communicates to both a x-mirror drive 8 and a y-mirror drive 9 to drive x-mirror 10 and y-mirror 11 in such a manner that a raster pattern is formed on the patient when the Red laser 3 and the IR laser 6 are coaxially projected thereon. X-mirror feedback 12 and y-mirror feedback 13 detect the positions of the x-mirror 10 and y-mirror 11, respectively, and communicates such information to the FPGA 1.

Top photodiode 23 and bottom photodiode 22 receive the IR Laser 6 reflected off the patient, converts the light into an analog signal which is provided to Top FE 25 and Bottom FE 24, and then to Top ADC 27 and bottom ADC 25, respectively. The top FE 25 and the bottom FE 24 are front end circuits that provide analog filtering, gain control and threshold of the analog signals. The Top ADC 27 and bottom ADC 26 are analog to digital converters that convert the analog signals to digital representations thereof to be communicated to the FPGA 1. Control lines are provided from the FPGA 1 to the top FE 25 and the bottom FE 24 to set parameters such as, for example, gain control and analog filtering.

From a mechanical standpoint, the red laser 3 and the IR laser 6 are co axially aligned and projected off of mirrors X-mirror 10 and Y-mirror 11 to form a pattern, such as for example, a raster pattern on the patient. The IR laser 6 reflects off the patient and is received by top photodiode 23 and photodiode 22. The reflected IR light contains information as to the location of the veins (IR light is absorbed by the blood in the veins and therefore the amount or reflected IR light is lower when the IR laser 6 is aimed at a vein. The FPGA 1 time sequentially receives in the signal form the top ADC 27 and the bottom ADC and can form two partial and/or full frame images of the reflected IR light (hereinafter a top channel data and a bottom channel data wherein the top channel data is received from the top ADC 27 and the bottom channel data is received from the bottom ADC). The FPGA 1 processes one or both of the partial and/or full image to detect and enhance the image of the veins. The enhanced image is time sequentially projected by the Red laser 3 onto the patient.

A CPLD is provided for controlling an LCD 19 with displays user information related to the operating status of the device. It also controls an audio 20 output to provide audible tones to the user. Finally the CPLD 18 controls the switches 21 on the unit for turning on and off the units as well as selecting user modes and entering data.

A microprocessor PIC MCU 17 is provided for receiving and monitoring the IR laser feedback 7 signal, the red laser feedback 4 signal, the x-mirror feedback 12 signal and the y-mirror feedback 13 signal. Since these signals are also provided to the FPGA 1, redundancy monitoring of the signals is provided by the PIC MCU 17. This is particularly important when regulatory requirements require redundant monitoring of the laser power and movement to comply with safety requirements. The PIC MCU 17 also monitors the device power management 14, the Li-ion Battery management 15 circuitry and the Li-ion Fuel gauge 16.

FIG. 2 shows an example of the signal processing flow of the FPGA.

FIG. 2 shows an embodiment of the signal processing algorithm of the FPGA of FIG. 1. As described with reference to FIG. 1, the image of the reflected IR laser 6 is time sequentially stored in the FPGA 1 as top channel data 30T and bottom channel data 30B.

The X-mirror 10 oscillates about a single axis to move the laser beam from the IR laser 6 to form a line. The beam moves first in one direction and then back in the other direction. It is critical that the left to right image data be in convergence with the right to left data. The top line correlator 31T measures the shift in the convergence of the top channel data 30T and supplies the information to the mirror convergence control 34. Similarly, the bottom line correlator 31B measures the shift in the convergence of the bottom channel data 30B and supplies the information to the mirror convergence control 34. The mirror convergence control 34 can adjust the control signals provided from the FPGA 1 to the x-mirror drive 8 so as to converge the data.

A top histogram 32T receives the top channel data 30T and generates a histogram based upon an entire frame of the top channel data 30T. Similarly, a bottom histogram 32B receives the top channel data 30B and generates a histogram based upon an entire frame of the bottom channel data 30B. The histograms contain information describing the characteristics of the images, including but not limited to contrast and intensity levels. The top histogram 32T and the bottom histogram 32B are provided to exposure control 35. Exposure control 35 communicates appropriate signals the IR laser drive 5 to adjust the power of the IR laser 6 on a frame by frame basis until the histograms indicate appropriate images. The exposure control 35 also communicates with the top FE 25 and bottom FE 24 to adjust parameters such as setting thresholds and setting electrical gain.

A top vein processing 33T block receives the top channel data 30T and performs image processing to detect vein patterns and provides the enhanced vein image to fused vein projection 36. Similarly, bottom vein processing 33B block receives the bottom channel data 30B and performs image processing to detect vein patterns and provides the enhanced vein image to fused vein projection 36. The fused vein projection 36 forms a single image and communicates the image to the alpha blended projection 38. The fused vein projection 36 can form the single image by merging the images from the top vein processing 33T and bottom vein processing 33B. Alternative, the fused vein projection 36 can simply select the best image received from the top vein processing 33T and the bottom vein processing 33B.

Alpha channel 37 forms an image that contains graphical data, such as text or characters. Alpha channel 37 and fused vein projection 36 are provided to alpha blended projection 38 with drives the IR laser drive 5 to display an image which is the combination of the fused vein projection 36 and the alpha channel 37.

Figure 3:
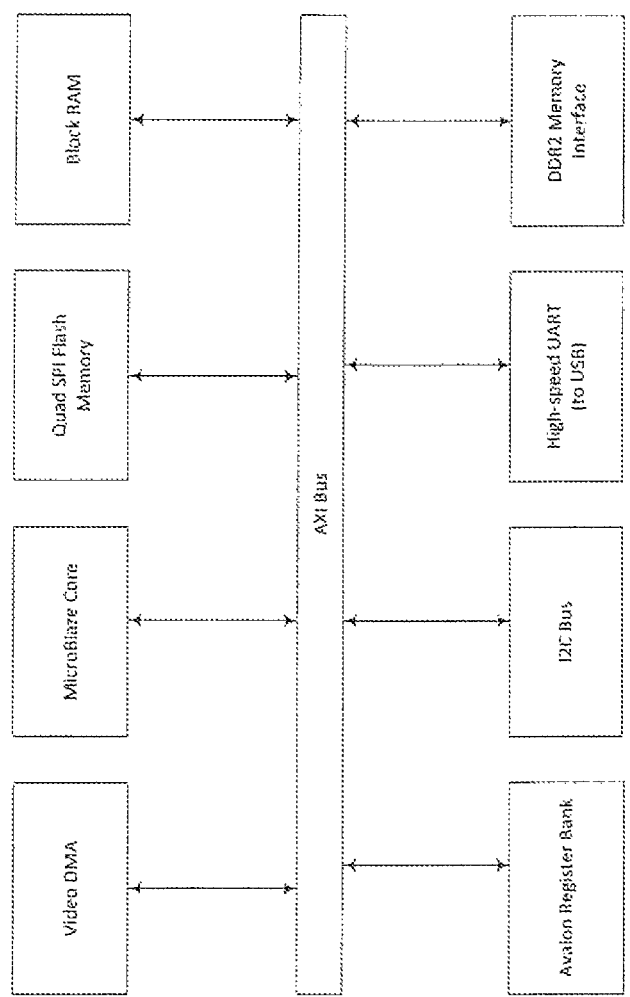
FIG. 3 shows the internal bus architecture of the FPGA.

FIG. 3 shows an example of the internal bus architecture of the FPGA

Figure 4:
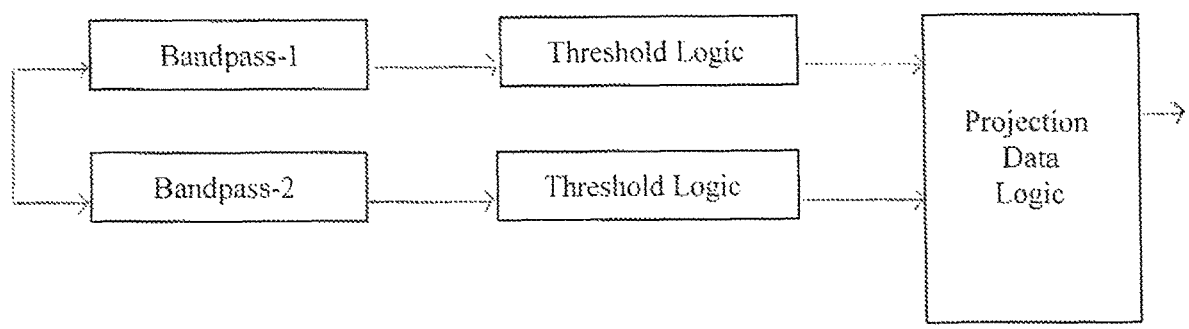
FIG. 4 shows details of the vein processing.

FIG. 4 shows details of the top vein processing 33T and bottom vein processing 33B.

Figure 5:
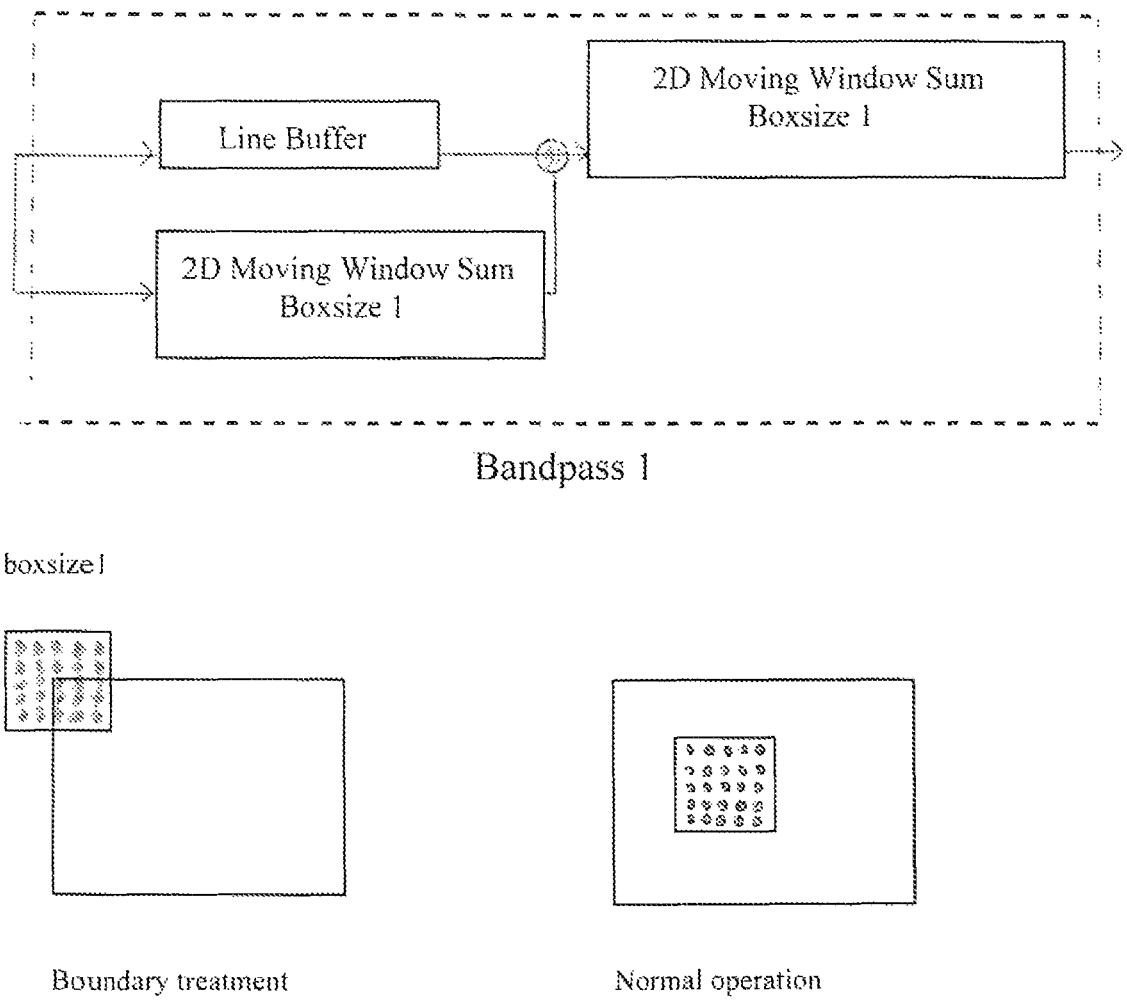
FIG. 5 shows the vein processing at the boundary of the image frames.

FIG. 5 shows the vein processing at the boundary of the image frames.

Figure 6:
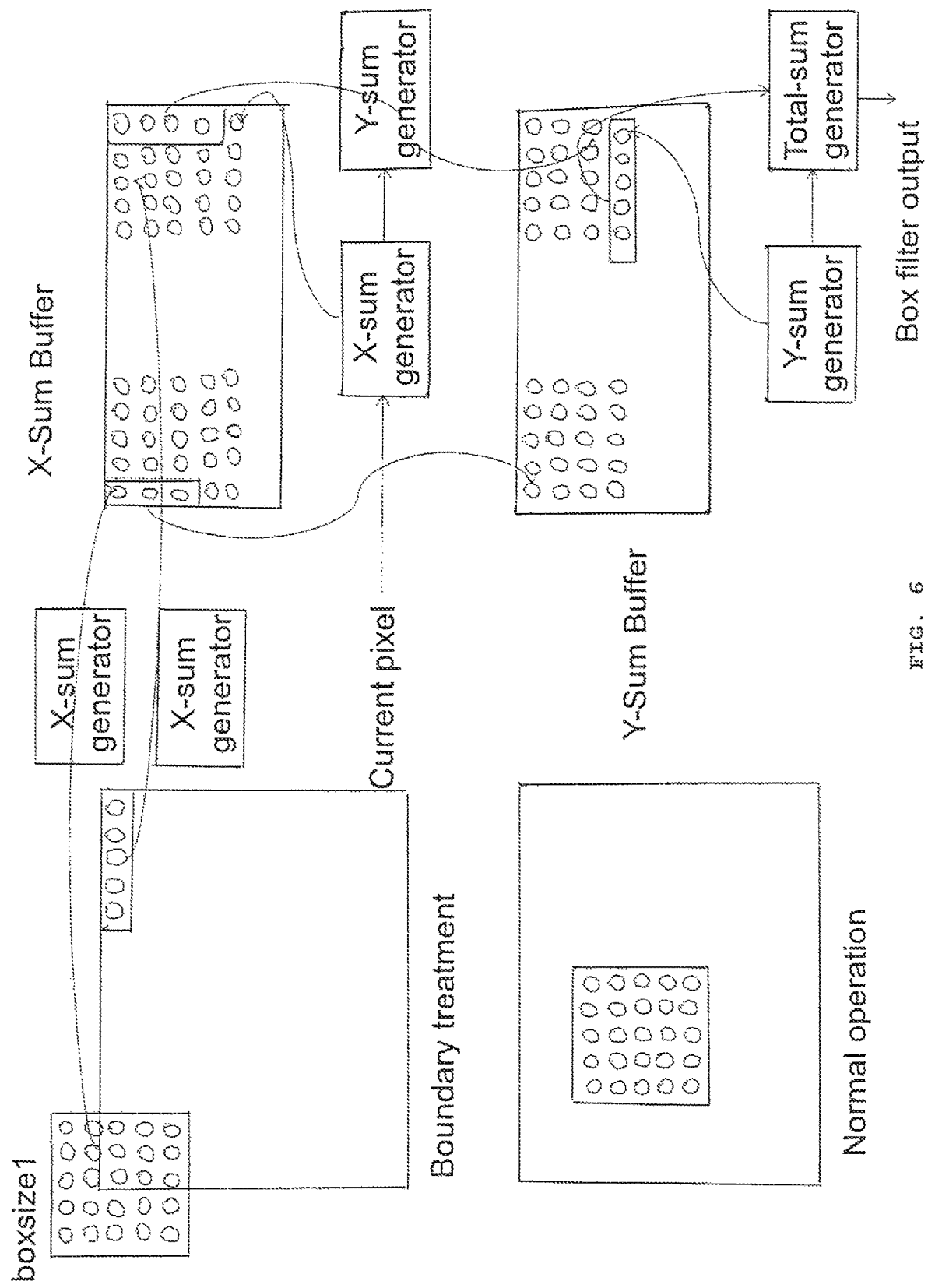
FIG. 6 shows further detail of the vein processing at the boundary of the image frames.

FIG. 6 shows further detail of the vein processing at the boundary of the image frames.

FIG. 7 shows the 2-D Moving Window Sum Generator.

FIG. 8 shows a X-sum generator.

What is claimed is:

1. An image capture device configured to detect, process, and project an image using a field programmable gate array (FPGA), said image capture device comprising:
   a first laser configured to output a beam of light at an infrared wavelength;
   a second laser configured to output a beam of light at a visible red wavelength;
   a combiner configured to combine said beams of light from said first and second lasers into a co-axial beam of light;
   an x-direction mirror configured to reflect said coaxial beam of light, and to be pivotable about a first axis, in a first direction and in a second direction;
   an x-direction mirror driver configured to drive said x-direction mirror to oscillate about said first axis, to cyclically reflect said coaxial beam of light in a line, in both said first and second directions;
   a y-direction mirror configured to reflect said line of light received from said x-direction mirror, and to be pivotable about a second axis, in a third direction and a fourth direction;
   a y-direction mirror driver configured to drive said y-direction mirror to oscillate about said second axis;
   a FPGA configured to control said x-direction mirror driver and said y-direction mirror driver to control said oscillations about said first and second axes to form a pattern of said red and infrared wavelengths of light;
   a feedback means configured for detecting a position of said x-direction mirror and said y-direction mirror, and for signaling said positions to said FPGA;
   a photodiode configured to receive the image formed from said infrared light, said photodiode further configured to convert the received image into an analog signal;
   wherein said second laser driver is further configured to receive said analog signal, and to drive said red laser to project the image using said analog signal;
   a line correlator configured to measure a shift in convergence between said line of light in said first direction and said second direction, for each said oscillation of said X-direction mirror;
   a mirror convergence control configured to receive said measured shift in convergence from said line correlator, and to adjust said control of said first mirror driver by said FPGA, for said line in said first direction to converge with said line in said second direction.

2. The image capture device according to claim 1, further comprising: a second feedback means configured for detecting said output of said first and second lasers, and for signaling said detected output to said FPGA, for said FPGA to control said output of said first and second lasers.

3. The image capture device according to claim 2, further comprising:
   an analog-to-digital converter configured to receive said analog signal from said photodiode, and to convert said analog signal into a digital image signal, and to communicate said digital image signal to said FPGA;
   wherein said FPGA is configured to receive and process said digital image signal and to output a processed image signal; and
   wherein said second laser driver is further configured to receive said processed image signal from said FPGA, and to drive said red laser to project said processed image using said x-direction mirror and said y-direction mirror.

4. The image capture device according to claim 3, wherein said photodiode comprises a top photodiode and a bottom photodiode each configured to receive a full frame of the image and to output a respective said analog signal.

5. The image capture device according to claim 4, further comprising:
   a top front end circuit and a bottom front end circuit, each configured to respectively receive said analog signals of said top and bottom photodiodes; said top and bottom front end circuits configured to control analog filtering, gain, and threshold of said respective analog signals;

wherein said analog-to-digital converter comprises a top analog-to-digital converter (ADC) and a bottom ADC configured to respectively receive said analog signals from said top and bottom front end circuits, and to convert said analog signals into respective digital image signals, and to communicate said respective digital image signals to said FPGA;

said FPGA further configured to receive each of said respective digital image signals from said top and bottom ADC, and to perform imaging processing within each of said respective images, to form respective enhanced images;

wherein said FPGA is further configured to form a single enhanced image signal from said respective enhanced images; and wherein said second laser driver is further configured to receive said single enhanced image from said FPGA, and to drive said red laser to project said enhanced single image using said x-direction mirror and said y-direction mirror.

6. The image capture device according to claim 5, wherein said single enhanced image is formed from:
   a merged signal formed by merging said respective digital image signals; or
   a selected best image signal selected from either of said respective digital image signals.

7. The image capture device according to claim 5, further comprising:
   a top histogram generator and a bottom histogram generator, each of said top and bottom histogram generators configured to generate a respective histogram of characteristics of said analog signals from said top and bottom photodiodes; and
   wherein said FPGA is further configured to receive and use said respective histograms to signal said infrared laser driver to adjust power to said infrared laser on a frame by frame basis until said histograms indicate a proper image.

8. The image capture device according to claim 7, wherein said histogram characteristics comprise contrast and intensity levels.

9. The image capture device according to claim 7, further comprising a CPLD configured to control an LCD to display an operating status of said system thereon.

10. The image capture device according to claim 9, wherein said CPLD is further configured to control an audio output to provide audible tones to a user.

11. The image capture device according to claim 10, wherein said CPLD is further configured to control one or more switches on said system for turning on and off said system, for selecting one or more user modes, and for entering data therein.

12. The image capture device according to claim 2, further comprising a microprocessor configured to redundantly receive and monitor said feedback signal for said first and second lasers, and said feedback signal for said X-direction mirror and Y-direction mirror, in conjunction with said FPGA.

13. An image capture device comprising:
   means for outputting and scanning a beam of light comprising an infrared wavelength and a visible red wavelength in a first and a second direction, for forming respective lines in said first and second directions, and for scanning said lines in a third direction and a fourth direction;
   a field programmable gate array (FPGA) configured to control said means for outputting and scanning to control said scanning in said first and second directions, and to control said scanning in said third and fourth directions, to form a pattern;
   a photodiode configured to receive an image formed from said scanned pattern of said infrared wavelength of light, said photodiode further configured to convert the image into an analog signal;
   wherein said means for outputting and scanning is further configured to receive said analog signal, and to scan said image using said visible red wavelength;
   a line correlator configured to measure a shift in convergence between said respective lines in said first and second directions;
   a mirror convergence control configured to receive said measured shift in convergence from said line correlator, and to adjust said control of said means for outputting and scanning by said FPGA, for said line in said first direction to converge with said line in said second direction.

14. The image capture device according to claim 13, further comprising:
   a first feedback means configured for detecting a position of said x-direction mirror and said y-direction mirror, and for signaling said positions to said FPGA;
   a second feedback means configured for detecting said output of said means for outputting and scanning, and for signaling said detected output to said FPGA, for said FPGA to control said output of said means for outputting and scanning;
   an analog-to-digital converter configured to receive said analog signal from said photodiode, and to convert said analog signal into a digital image signal, and to communicate said digital image signal to said FPGA;
   wherein said FPGA is configured to receive and process said digital image signal and to output a processed image signal; and
   wherein said means for outputting and scanning is further configured to receive said processed image from said FPGA, and to scan said processed image using said red wavelength.

15. The image capture device according to claim 13, wherein said photodiode comprises a top photodiode and a bottom photodiode each configured to receive a full frame of said image and to output a respective said analog signal.

16. The image capture device according to claim 15, further comprising:
   a top front end circuit and a bottom front end circuit, each configured to respectively receive said analog signals of said top and bottom photodiodes; said top and bottom front end circuits configured to control analog filtering, gain, and threshold of said respective analog signals;
   wherein said analog-to-digital converter comprises a top analog-to-digital converter (ADC) and a bottom ADC configured to respectively receive said analog signals from said top and bottom front end circuits, and to convert said analog signals into respective digital image signals, and to communicate said respective digital image signals to said FPGA;
   said FPGA further configured to receive each of said respective digital image signals from said top and bottom ADC, and to perform imaging processing within each of said respective images, to form respective enhanced images;

wherein said FPGA is further configured to form a single enhanced digital image from said respective enhanced images; and wherein said means for outputting and scanning is further configured to receive said single enhanced image from said FPGA, and to scan said single enhanced image using said visible red wavelength.

17. The image capture device according to claim 16, wherein said single enhanced image comprises:
   a merged signal formed by merging said respective digital image signals; or
   a selected best image signal selected from either of said respective digital image signals.

18. The image capture device according to claim 16, further comprising:
   a top histogram generator and a bottom histogram generator, each of said top and bottom histogram generators configured to generate a respective histogram of characteristics of said analog signals from said top and bottom photodiodes; and
   wherein said FPGA is further configured to receive and use said respective histograms to adjust power to said means for outputting and scanning on a frame by frame basis until said histograms indicate a proper image.

19. The image capture device according to claim 18, wherein said histogram characteristics comprise contrast and intensity levels.

20. The image capture device according to claim 13, further comprising a microprocessor configured to redundantly monitor and control said means for outputting and scanning to control said scanning in said first and second directions, and said scanning in said third and fourth directions, to form a raster pattern.

21. An image capture device comprising:
   means for outputting and scanning a beam of light comprising an infrared wavelength and a visible red wavelength in a first and a second direction, for forming respective lines in said first and second directions, and for scanning said lines in a third direction and a fourth direction;
   an electronic component configured to control said means for outputting and scanning to control said scanning in said first and second directions, and to control said scanning in said third and fourth directions, to form a pattern;
   a photodiode configured to receive an image formed from said scanned pattern of said infrared wavelength of light, said photodiode further configured to convert the image into an analog signal;
   wherein said means for outputting and scanning is further configured to receive said analog signal, and to scan said image using said visible red wavelength;
   a line correlator configured to measure a shift in convergence between said respective lines in said first and second directions;
   a mirror convergence control configured to receive said measured shift in convergence from said line correlator, and to adjust said control of said means for outputting and scanning by said electronic component, for said line in said first direction to converge with said line in said second direction.

22. The image capture device according to claim 21, further comprising:
   a feedback means configured for detecting said output of said means for outputting and scanning, and for signaling said detected output to said electronic component, for said electronic component to control said output of said means for outputting and scanning;
   an analog-to-digital converter configured to receive said analog signal from said photodiode, and to convert said analog signal into a digital image signal, and to communicate said digital image signal to said electronic component;
   wherein said electronic component is configured to receive and process said digital image signal and to output a processed image signal; and
   wherein said means for outputting and scanning is further configured to receive said processed image from said electronic component, and to scan said processed image using said red wavelength.

23. The image capture device according to claim 22, wherein said photodiode comprises a top photodiode and a bottom photodiode each configured to receive a full frame of said image and to output a respective said analog signal.

* * * * *